United States Patent [19]

Arme, Jr.

[11] Patent Number: 5,080,109
[45] Date of Patent: Jan. 14, 1992

[54] METHOD AND APPARATUS FOR ANALYSIS OF POSTURAL ABNORMALITIES

[76] Inventor: Joseph F. Arme, Jr., 519 E. El Camino Dr., Phoenix, Ariz. 85020

[21] Appl. No.: 655,783

[22] Filed: Feb. 15, 1991

[51] Int. Cl.$^5$ ............................................... A61B 5/03
[52] U.S. Cl. ...................................... 128/782; 33/515
[58] Field of Search ..................... 128/774, 781, 782; 33/511, 512, 515

[56] References Cited

U.S. PATENT DOCUMENTS

| | | | |
|---|---|---|---|
| 4,416,293 | 11/1983 | Anderson et al. | 128/782 |
| 4,571,834 | 2/1986 | Fraser et al. | 128/782 |
| 4,600,012 | 7/1986 | Kohayakawa et al. | 128/781 |
| 4,602,280 | 7/1986 | Maloomian | 358/93 |
| 4,699,156 | 10/1987 | Gracovetsky | 128/781 |
| 4,760,851 | 8/1988 | Fraser et al. | 128/774 |
| 4,922,925 | 5/1990 | Crandall et al. | 128/782 |

FOREIGN PATENT DOCUMENTS

0245098 11/1987 European Pat. Off. .

*Primary Examiner*—Max Hindenburg
*Attorney, Agent, or Firm*—Cahill, Sutton & Thomas

[57] ABSTRACT

Method and apparatus for diagnosing posture abnormalities includes a video camera, a video display terminal, a subject platform positioned between the camera and the terminal so that the subject can view the terminal. A computer is employed to freeze a video image of the subject on said terminal so that an operator can obtain data regarding the relative positions of landmarks on said image using a light pen. The computer analyzes the landmark position data and generates a diagnosis of postural abnormalities of the subject. The method and apparatus may also employ a weight scale on the subject platform for transmitting data to the computer regarding the weight distribution on the feet of the subject.

10 Claims, 2 Drawing Sheets

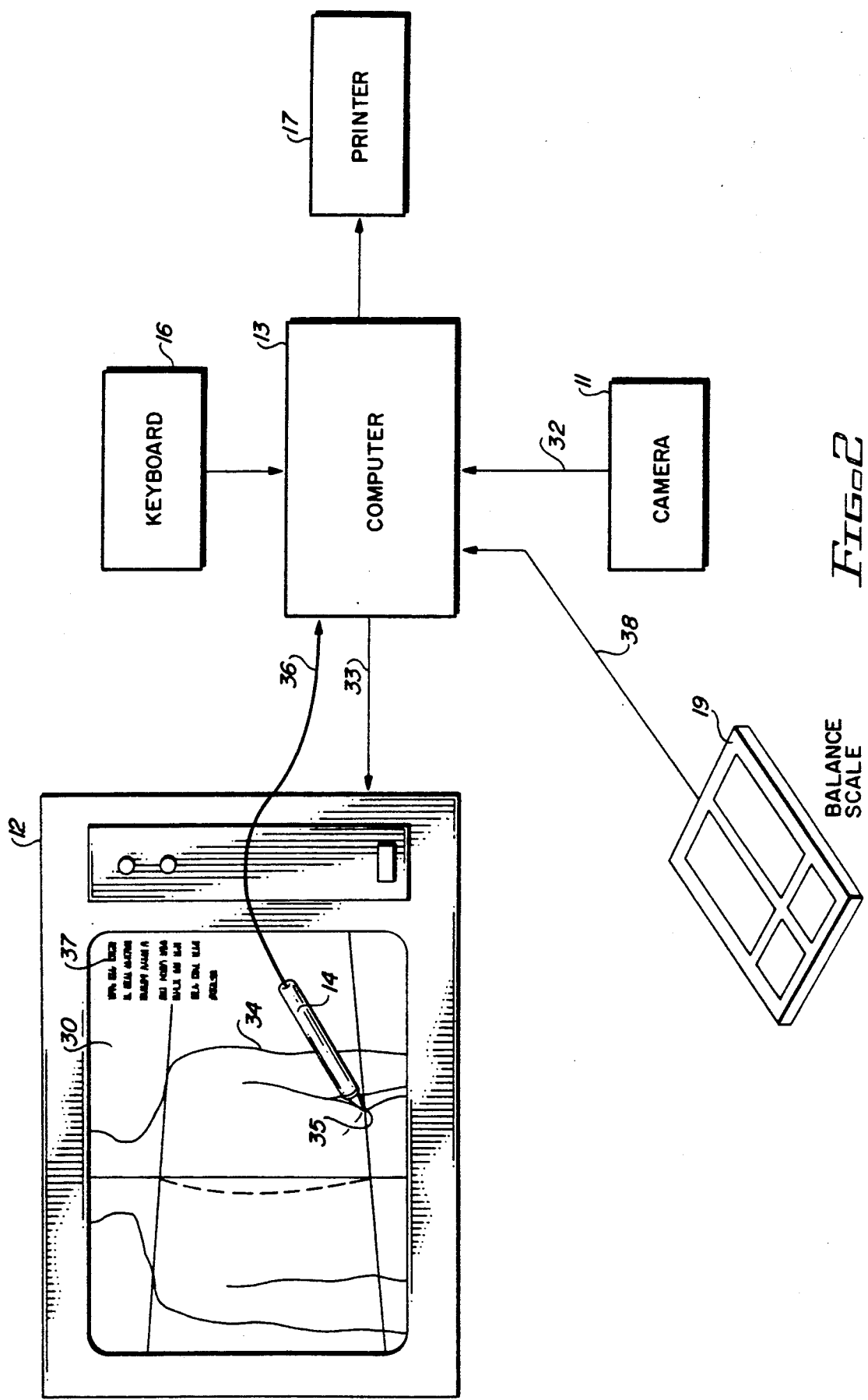

METHOD AND APPARATUS FOR ANALYSIS OF POSTURAL ABNORMALITIES

TECHNICAL FIELD

This invention is concerned with postural analysis for the detection and correction of skeletal abnormalities, such as scoliotic spinal curvature, insufficient spinal flexibility, imbalance and leg length deficiencies.

BACKGROUND ART

Postural abnormalities can exhibit a variety of undesirable symptoms, such as, for example, low back pain, spinal curvature, scoliosis, arthrosis, spinal disc degeneration, organ displacement, and hip and knee joint degeneration. And, it is well known that spinal misalignment can result in the appearance of undesirable and uncomfortable symptoms at locations throughout the body and limbs.

Because of the variety of postural abnormalities that can be experienced by human subjects, accurate analysis and diagnosis is required if a correct and effective treatment is to be rendered.

Skilled physicians often can perform diagnosis of postural deformities by visual observation of the subject. This is particularly true when the skeletal asymmetries are prominent.

However, in the case of slight postural abnormalities, visual inspection may lead to an incorrect diagnosis or complete failure to detect the abnormality.

So, over time, a number of different techniques and pieces of apparatus have been put forth to assist the physician in making his diagnosis. Most of these have involved measuring the relative position of various palpable landmarks on the subject's body.

The simplest diagnostic apparatus usually takes the form of a rectangular frame with fixed or movable grid lines stretched across it. Displacement of the landmarks on the subject are more apparent when the subject is viewed through the grid. One such instrument, namely the SAM spinal analysis machine produced by S.A.M. of Las Vegas, Nev., also includes a mechanical leveling platform for measuring leg length differences.

A somewhat more sophisticated apparatus for measuring short leg syndrome and consequential postural abnormalities is represented by the Dynatronic Equalizer brand analysis machine produced by Dynatronics of Salt Lake City, Utah. This device couples the grid frame with a motorized weight balance platform and digital readouts.

Faro Medical Technologies, Montreal, Canada, produces a skeletal analysis system under the trademark "METRECOM" which employs a digitizer to measure the position of a point, or group of points, on the applicant's body in three-dimensional space. The digitizer includes a plurality of rotatable transducers and a plurality of link members linking the transducers. Movement of a tip at the free end of the digitizer causes the transducers to generate signals which are transmitted to and analyzed by a computer. Operation of this apparatus is described in U.S. Pat. No. 4,571,834, granted Feb. 25, 1986, to G. A. Fraser, et. al., for "Knee Laxity Evaluation and Motion Module/Digitizer Arrangement", and U.S. Pat. No. 4,760,851, granted Aug. 2, 1988, to G. A. Fraser, et. al., for "Three-Dimensional Digitizer for Skeletal Analysis".

U.S. Pat. No. 4,922,925, granted May 8, 1990, to R. E. Crandall, et. al., for "Computer Based Upper Extremity Evaluation System" discloses a similar system for evaluation of the performance of the joints of the hand, the wrist, and the elbow.

One problem associated with the four machine techniques described above is that the subject must remain absolutely motionless during the examination. And, this is difficult for most subjects. Only a skilled operator acting swiftly is likely to produce reliable data that is useful as a basis for diagnosis.

European patent application Serial No. 87304069.5, published Nov. 11, 1987, as Publication No. 0 245 098 A2 for Teijim Limited of Osaka, Japan, discloses the use of a digitizer board for extracting positional data from an X-ray image of vertebrae. The digitized data is fed to a computer for analysis. X-rays are invasive and many subjects prefer not to be subjected to X-rays.

It has also been proposed to employ video systems for the analysis of postural abnormalities of human subjects. Representative of this art are U.S. Pat. No. 4,600,012, granted July 15, 1986, to Y. Kohayakawa, et. al., for "Apparatus for Detecting Abnormality in Spinal Column" and U.S. Pat. No. 4,699,156, granted Oct. 13, 1987, to S. Gracovetsky for "Non-invasive Method and Equipment for the Detection of Torsional Injuries in the Human Spine of a Patient". The diagnosis performed by the apparatus of the Kohayakawa patent is based solely on measuring the difference in heights of the right and left shoulders of the subject and is of only limited value in determining the treatment required. The diagnosis proposed in the Gracovetsky patent is also of limited value because it is concerned only with measuring the position of vertebrae of the lumbar curve.

Video techniques have also been employed in podiatric diagnoses, as evidenced by U.S. Pat. No. 4,416,293, granted Nov. 22, 1983, to B. V. Anderson, et. al. for "Method and Apparatus for Recording Gait Analysis in Podiatric Diagnosis and Treatment" and in weight loss/gain evaluation as disclosed in U.S. Pat. No. 4,602,280, granted July 22, 1986, to L. G. Maloomian for "Weight and/or Measurement Reduction Preview System". Neither of these techniques is capable of performing a comprehensive evaluation of postural abnormalities.

There continues to be a need for apparatus and a method for non-invasive evaluation of postural abnormalities giving reliable diagnostic results.

DISCLOSURE OF THE INVENTION

This invention employs a video camera and a video display terminal in combination with a computer having the capability to freeze an image on the display screen. The region of the subject's body which is to be evaluated is thus displayed as a still figure on the video screen. The operator using a light-sensitive pen in conjunction with the video display screen generates data regarding the relative positions of landmarks on the displayed image. This positional data is supplied to the computer which analyzes the data and generates a diagnosis based thereon. The video display and the light pen operations performed therewith are preferably within the view of the subject so that he or she may participate in the evaluation procedure.

BRIEF DESCRIPTION OF THE DRAWINGS

The invention is described in greater detail hereinafter by reference to the accompanying drawings, wherein:

FIG. 2 is a block diagram illustrating the interaction of the several components of the invention.

BEST MODE FOR CARRYING OUT THE INVENTION

Figure 1:
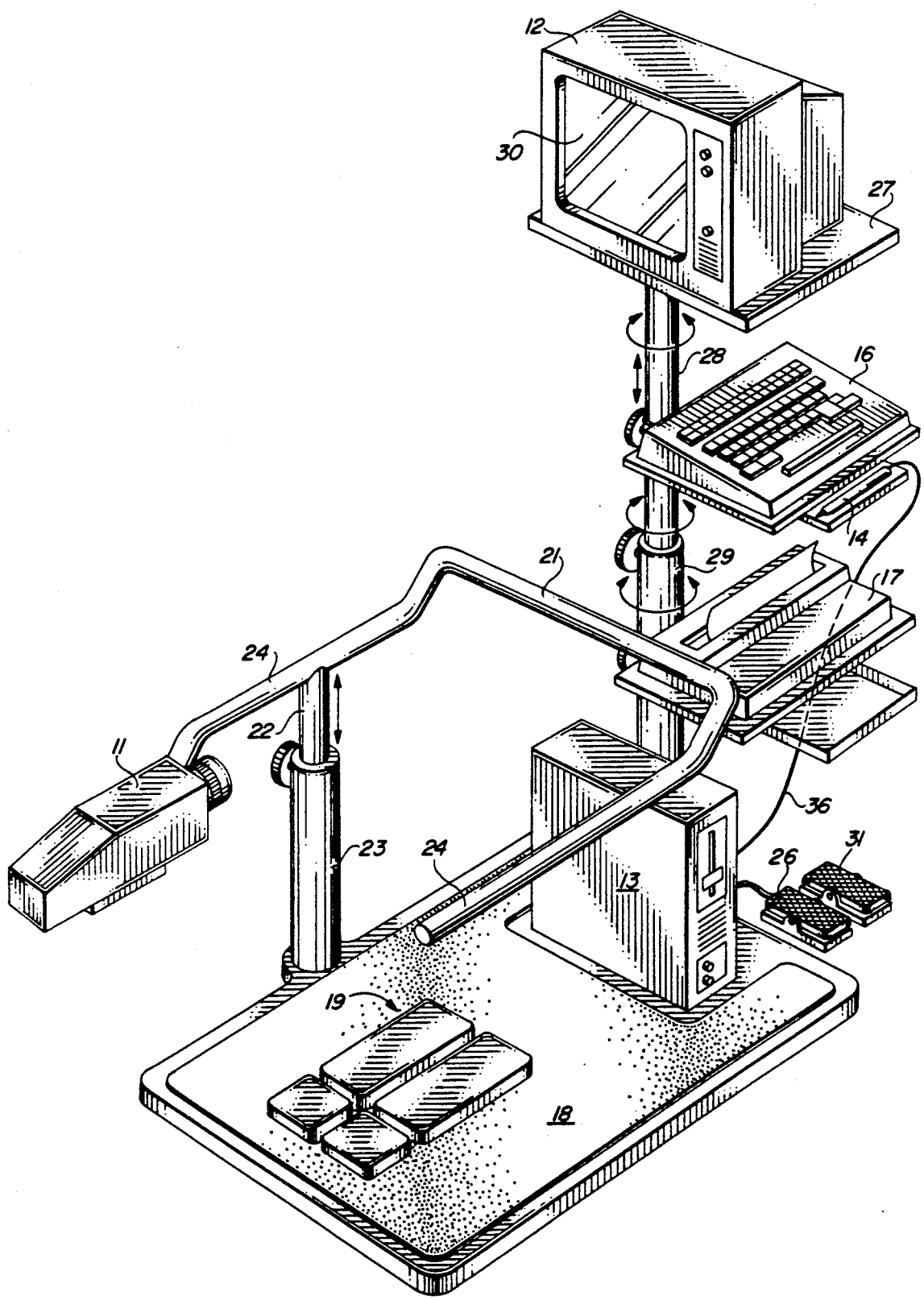
FIG. 1 is a perspective view of the apparatus employed to practice the invention.

The principal components of the diagnostic apparatus of this invention are illustrated in FIG. 1 and include a video camera 11 for capturing the image of a subject (not shown) to be evaluated, a video display terminal 12 for displaying the image, a computer 13 for controlling, among other things, the presentation of the image on the display terminal 12, and a light-sensitive pen 14 for extracting positional data from the image on the display terminal screen. The apparatus also preferably includes a keyboard 16 for imparting information to and issuing operating instructions to the computer 13. A printer 17 is provided for producing narrative reports of the diagnoses generated by the computer 13.

The subject to be evaluated stands on a platform 18 between the camera 11 and the video display terminal 12. Platform 18 may have positioned thereon a weight scale arrangement 19 for measuring the distribution of weight on the front and rear portions of each foot of the subject.

Video camera 11 is preferably carried by one leg of a U-shaped frame 21. Frame 21 is affixed to a vertical support column 22 which is movable up and down in a cylindrical stand 23 mounted on platform 18. Vertical adjustment of the position of camera 11 permits examination of selected regions of the body of the subject standing on platform 18. This adjustment can also compensate for individuals with different heights. The arms 24 of frame 21 assist the subject in getting on and off the platform 18.

If desired, movement of frame 21 and camera 11 can be motorized under control of a foot pedal switch 26.

A similar support structure is provided for the video display terminal 12 and the keyboard 16. Terminal 12 rests atop a platform 27 supported by column 28 that is rotatable and vertically movable within a cylindrical stand 29 mounted on platform 18. Vertical adjustment of the position of terminal 12 and keyboard 16 is provided so that the height of the terminal 12 is convenient for viewing by the subject and the operator and the keyboard 16 is convenient to the operator. Rotation of column 28 in stand 29 permits the display terminal to be swiveled so that it can be viewed simultaneously by the subject and the operator and accessible to the operator for use of the light pen 14 against terminal screen 30 as is explained hereinafter. Vertical movement of the terminal 12 and the keyboard 16 can also be motorized under control of foot pedal switch 31.

Printer 17 can be mounted in any convenient location, such as on the vertical stand 29.

The method of analyzing postural abnormalities utilizing the apparatus of this invention is best understood by reference to FIG. 2. As there shown, the video camera 11 has been positioned to view the upper torso of the subject from the rear. The camera 11 sends a picture signal, represented by line 32, to the computer 13 which, in turn, sends a video signal, represented by line 33, to the video display terminal which displays the image 34 which has been captured by the camera 11.

In accordance with this invention, the computer 13 contains an image capture board (not shown) which is capable of transmitting a real-time video signal 33 so that the image 34 presented on display terminal screen 30 moves as the subject moves in front of the camera 11. The image capture board also has the capability of capturing and storing video signal information so as to freeze the image 34 on the display terminal screen 30. In other words, a still image is caused to appear on the terminal screen, even though the subject may continue to move in front of the camera. The image capture board may be activated to create a still image 34 on signal from the manually manipulated keyboard 16 or the computer 13 may be programmed to activate the image capture board at a specific point in the examination sequence.

The still image 34 appearing on the screen 30 of the video display terminal is utilized to obtain data regarding the relative positions of several landmarks on the body represented by the image. There are several advantages to employing a video image for this purpose. First, unlike X-ray images employed in a similar manner in the past, the video system is non-invasive of the subject. Secondly, the subject is free to move comfortably during the positional data acquiring sequence and this freedom contrasts with the strict requirements of some of the prior measuring techniques discussed in the background art section above. Furthermore, presentation of the video image within the view of the subject allows the subject to participate and become a part of the examination procedure. Again, this contrasts with prior procedures in which measurements were taken from behind and out of the view of the subject. And, of course, there are no time constraints on the operator so he or she can acquire the landmark position data in an unhurried manner. In all, the system and examination procedure constitute a "user friendly" environment for both the subject and the operator.

The preferred technique for obtaining data regarding the relative positions of the landmarks on image 34 involve the use of the light-sensitive pen 14 against the video screen 30. When light pen 14 has its acquisition tip placed against the glass screen 30 at a landmark point 35, a light-sensitive element (not shown) within the pen will be triggered when the raster scanning electron beam creating image 34 passes beneath the tip of the pen and causes the tube coating on the inside of the screen at that point to luminesce. A signal from the light-sensitive pen 14 is supplied over lead 36 to the computer which combines this signal with the raster scan information contained therein and records in its memory the location of that particular landmark point 35.

The operator next moves light pen 14 to another landmark and its position is noted by the computer 13. When positional data has been acquired from a previously determined number of landmarks, the computer 13 utilizes a program therein to analyze the position data and diagnose the postural condition of the subject. Preferably, the programming of the computer 13 is sufficient to permit a narrative report to be created through the use of the printer 17.

If desired, the computer 13 an also be programmed to prompt, i.e. generate instructional messages for, the operator as to the identity and sequence of access of the landmarks on image 34. Such messages may be caused to appear on the video display screen 30 as indicated at 37.

Data from the balance scale 19 regarding the weight distribution on the subject's feet is fed over a line 38 to the computer 13 for analysis together with or separately from the data regarding the landmark positions.

The computer is also capable of storing in its memory for inclusion in the narrative report from printer 17 statistical information entered via keyboard 16. Such information may include the subject's name, sex, age, the date of the examination, the test number, etc.

The method and apparatus of this invention are quite versatile. With appropriate menus and programs for the computer 13, it is possible to perform a variety of postural evaluations.

For example, a complete plumb line analysis displaying a digitized video picture of the entire body in lateral and postero-anterior views can be performed. Graphic and narrative output of all asymmetries, displacements and standard angles of reference can be generated.

Also, rapid visualization and analysis of scoliotic curvatures including calculation of the Cobb angles and display of the end vertebrae can be produced. Multiple level rib hump measurements are obtainable for back contour measurements.

Full narrative reports can be made available following any of these examinations. Reports and analysis of data obtained by progressive examinations can be utilized to validate treatment protocol and predict return of normal function.

What is claimed is:

1. A method of body posture analysis comprising the steps of:
    (a) creating a video image of that portion of the body to be analyzed utilizing a video camera and a video display terminal;
    (b) causing the image to freeze in said display to present a still image of the said portion of the body;
    (c) generating data regarding the relative positions of a plurality of landmarks on said still image utilizing a light-sensitive pen and said video display; and
    (d) analyzing the landmark position data and generating from that analysis a diagnosis of the postural abnormalities of said body.

2. A method of posture analysis as set forth in claim 1, performed on a human subject and further comprising presentation of the video display for visual perception by the subject during generation of said landmark position data.

3. A method of posture analysis as set forth in claim 2, further comprising generating data regarding the weight distribution on the feet of the subject, analyzing the weight distribution data and generating therefrom a diagnosis of posture abnormalities of the subject.

4. A method of posture analysis as set forth in claim 1, further comprising the generation of instructions to an operator for manipulation of the light pen.

5. A method of posture analysis as set forth in claim 1, further comprising the step of generating a narrative presentation of the diagnosis.

6. Apparatus for analyzing the posture of a subject, said apparatus comprising a video camera, a video display terminal, a subject platform positioned between said camera and said display terminal, a computer connected to said camera and said display terminal, means for issuing instructions to said computer, one such instruction being to cause said display terminal to display a still image of the subject, a light-sensitive pen operated in conjunction with said display terminal and said computer for generating data regarding the relative positions of a plurality of landmarks on the still image on said display terminal, said computer including means for analyzing said landmark position data and generating a diagnosis of postural abnormalities of the subject.

7. The posture analyzing apparatus of claim 6, further comprising a weight scale on said subject platform for transmitting data to said computer regarding the weight distribution on the feet of the subject.

8. The posture analyzing apparatus of claim 6, further comprising means for presenting a narrative of the diagnosis generated by said computer.

9. The posture analyzing apparatus of claim 7, including means in said computer for generating a diagnosis of postural abnormalities of the subject on the basis of data received from said weight scale.

10. The posture analyzing apparatus of claim 6, further comprising means in said computer for generating commands for instructing an operator of the apparatus regarding the landmarks to be addressed with said light pen.

* * * * *